US007806906B2

(12) United States Patent
Don Michael

(10) Patent No.: US 7,806,906 B2
(45) Date of Patent: Oct. 5, 2010

(54) VASCULAR FILTER WITH IMPROVED STRENGTH AND FLEXIBILITY

(76) Inventor: T. Anthony Don Michael, 4109 Sill Pl., Bakersfield, CA (US) 93306

( * ) Notice: Subject to any disclaimer, the term of this patent is extended or adjusted under 35 U.S.C. 154(b) by 731 days.

(21) Appl. No.: 11/745,839

(22) Filed: May 8, 2007

(65) Prior Publication Data
US 2009/0024153 A1  Jan. 22, 2009

(51) Int. Cl.
*A61B 17/22* (2006.01)
(52) U.S. Cl. ............................... 606/159; 606/200
(58) Field of Classification Search .......... 606/108, 606/110, 113, 114, 127, 159, 194, 200; 623/1.11, 623/1.12, 1.35
See application file for complete search history.

(56) References Cited

U.S. PATENT DOCUMENTS

| | | | | |
|---|---|---|---|---|
| 6,022,336 A | * | 2/2000 | Zadno-Azizi et al. | 604/101.05 |
| 6,096,053 A | * | 8/2000 | Bates | 606/159 |
| 6,156,055 A | * | 12/2000 | Ravenscroft | 606/206 |
| 6,295,989 B1 | * | 10/2001 | Connors, III | 128/898 |
| 6,423,032 B2 | * | 7/2002 | Parodi | 604/103.07 |
| 6,582,448 B1 | * | 6/2003 | Boyle et al. | 606/200 |
| 2005/0131453 A1 | * | 6/2005 | Parodi | 606/200 |
| 2006/0259066 A1 | * | 11/2006 | Euteneuer | 606/200 |

* cited by examiner

*Primary Examiner*—Anhtuan T Nguyen
*Assistant Examiner*—Elizabeth Houston
(74) *Attorney, Agent, or Firm*—Browdy and Neimark, PLLC

(57) ABSTRACT

A method and apparatus for treating a patient having an obstruction in a first blood vessel through which blood normally flows in a given direction, at a location downstream of a branch point where the first blood vessel and, a second blood vessel branch off from a main blood vessel, by: blocking blood flow in the main blood vessel at a point upstream of the branch point; inserting into the second blood vessel a first filter adapted to pass blood while trapping debris resulting from removal of the obstruction; inserting an obstruction removal assembly into the first blood vessel and operating the assembly to at least partially break up the obstruction and produce debris; withdrawing the obstruction removal assembly from the patient's body; and then inserting into the first blood vessel a filter adapted to pass blood while trapping debris; then restoring blood flow in the main blood vessel.

6 Claims, 8 Drawing Sheets

VASCULAR FILTER WITH IMPROVED STRENGTH AND FLEXIBILITY

BACKGROUND OF THE INVENTION

This invention relates to medical devices, such as vascular filters to be used in a body lumen, such as a blood vessel, with improved strength and flexibility. A filter according to the invention includes a proximal frame section, a distal section and a flexible thin membrane with perfusion holes of a diameter that allows blood to pass, but prevents the movement of emboli downstream.

Both sections can be collapsed into a small diameter delivery catheter and expanded upon release from this catheter. The membrane has a proximal entrance mouth, which can be expanded, or deployed, substantially to the same size as the body lumen. It is attached to the proximal frame section, which has the function to keep the mouth of the membrane open and prevent the passing of emboli between the body lumen wall and the edge of the filter mouth.

In order to have a good flexibility, the membrane is made extremely thin. Normally this would create the risk that the membrane could tear easily, which could cause problems because emboli and pieces of the membrane would then be carried downstream from the filter site.

U.S. Pat. No. 5,885,258 discloses a retrieval basket for catching small particles, made from a slotted tube preferably made of Nitinol, a titanium nickel shape memory alloy. The pattern of the slots allows expansion of the Nitinol basket and by shape setting (heat treatment in the desired unconstrained geometry) this basket is made expandable and collapsible by means of moving it out or into a surrounding delivery tube.

In principle, a distal filter is made of such an expandable frame that defines the shape and enables placement and removal, plus a filter membrane or mesh that does the actual filtering work.

Sometimes the expandable frame and the mesh are integrated and made from a single material, for example Nitinol, as disclosed in U.S. Pat. No. 6,383,205 or US Published Application No. 2002/0095173. These filters do not have a well-defined and constant size of the holes where the blood flows through, because of the relative movement of the filaments in the mesh. This is a disadvantage, because the size of emboli can be very critical, e.g. in procedures in the carotid arteries. Further the removal of such a filter, accompanied by a reduction of the diameter, may be critical because emboli can be squeezed through the mesh openings with their changing geometry.

A much better control of the particle size is achieved with a separate membrane or filter sheath, which has a well-defined hole pattern with for example holes of 100 microns, attached to a frame that takes care of the correct placement and removal of the filter.

WO 00/67668 discloses a Nitinol basket that forms the framework of the filter, and a separate polymer sheath is attached around this frame. At the proximal side, the sheath has large entrance ports for the blood and at the distal side a series of small holes filters out the emboli. This system, however, has some major disadvantages. First of all, the closed basket construction makes this filter frame rather rigid and therefore it is difficult to be used in tortuous arteries. At a curved part of an artery, it may even not fit well against the artery wall and will thus cause leakage along the outside of the filter.

Another disadvantage of such filters is there is a high risk of squeezing-out the caught debris upon removal, because the struts of the framework force the debris back in the proximal direction, while the volume of the basket frame decreases when the filter is collapsed. Further the construction makes it very difficult to reduce the profile upon placement of the filter. This is very critical, because these filters have to be advanced through critical areas in the artery, where angioplasty and/or stenting are necessary. Of course the catheter that holds this filter should be as small as possible then. In the just described filter miniaturization would be difficult because at a given cross section there is too much material. The metal frame is surrounded by polymer and in the center there is also a guide wire. During angioplasty and stenting, the movements of the guide wire will create further forces that influence the position and shape of the filter, which may cause problems with the proper sealing against the artery wall. This is also the case in strongly curved arteries.

In U.S. Pat. No. 6,348,062, a frame is placed proximal and a distal polymer filter membrane has the shape of a bag, attached to one or more frame loops, forming an entrance mouth for the distal filter bag. Here the bag is made of a very flexible polymer and the hole size is well defined. Upon removal, the frame is closed, thus closing the mouth of the bag and partly preventing the squeezing-out of debris. This is already better than for the full basket design, which was described above, where the storage capacity for debris of the collapsed basket is relatively small. The filter bag is attached to the frame at its proximal end and sometimes to a guide wire at its distal end. Attachment to the guide wire can be advantageous, because some pulling force may prevent bunching of the bag in the delivery catheter.

It may be clear that it is easier to pull a flexible folded bag through a small diameter hole, than to push it through. However, the deformation of the bag material should stay within certain limits.

If the filter is brought into a delivery sheath of small diameter, collapsing the frame and pulling the bag into the delivery sheath causes rather high forces on the connection sites of filter to frame and/or guide wire. While the metal parts of the frame slide easily through such a delivery sheath, the membrane material may have the tendency to stick and in the worst case it may even detach from the frame and tear upon placement or during use, because of too much friction, unlimited expansion, crack propagation etc.

The connection of the filter bag to the frame is rather rigid, because of the method of direct attachment. Additional flexibility, combined with a high strength attachment spot would also be advantageous.

Methods for making kink resistant reinforced catheters by embedding wire ribbons are described in PCT/US93/01310. There, a mandrel is coated with a thin layer of encapsulating material. Then, a means (e.g. a wire) for reinforcement is deposited around the encapsulating material and eventually a next layer of encapsulating material is coated over the previous layers, including the reinforcement means. Finally the mandrel is removed from the core of the catheter.

Materials for encapsulating are selected from the group consisting of polyesterurethane, polyetherurethane, aliphatic polyurethane, polyimide, polyetherimide, polycarbonate, polysiloxane, hydrophilic polyurethane, polyvinyls, latex and hydroxyethylmethacrylate.

Materials for the reinforcement wire are stainless steel, MP35, Nitinol, tungsten, platinum, Kevlar, nylon, polyester and acrylic. Kevlar is a Dupont product, made of long molecular highly oriented chains, produced from poly-paraphenylene terephalamide. It is well known for its high tensile strength and modulus of elasticity.

In U.S. application Ser. No. 09/537,461 the use of polyethylene with improved tensile properties is described. It is stated that high tenacity, high modulus yarns are used in medical implants and prosthetic devices. Properties and production methods for polyethylene yarns are disclosed.

U.S. Pat. No. 5,578,374 describes very low creep, ultra high modulus, low shrink, high tenacity polyolefin fibers having good strength retention at high temperatures, and methods to produce such fibers. In an example, the production of a poststretched braid, applied in particularly woven fabrics is described.

In US Published Application No. 2001/0034197, oriented fibers are used for reinforcing an endless belt, comprising a woven or non-woven fabric coated with a suitable polymer of a low hardness polyurethane membrane, in this case to make an endless belt for polishing silicon wafers. Examples are mentioned of suitable yarns like meta- or para-aramids such as KEVLAR, NOMEX OR TWARON; PBO or its derivatives; polyetherimide; polyimide; polyetherketone; PEEK; gel-spun UHMW polyethylene (such as DYNEEMA or SPECTRA); or polybenzimidazole; or other yarns commonly used in high-performance fabrics such as those for making aerospace parts. Mixtures or blends of any two or more yarns may be used, as may glass fibers (preferably sized), carbon or ceramic yarns including basalt or other rock fibers, or mixtures of such mineral fibers with synthetic polymer yarns. Any of the above yarns may be blended with organic yarns such as cotton.

BRIEF SUMMARY OF THE INVENTION

The present invention provides a method and apparatus for treating a patient having an obstruction on a wall of a first blood vessel through which blood normally flows in a given direction, at a location downstream of a branch point where the first blood vessel and, a second blood vessel branch off from a main blood vessel, by:

blocking blood flow in the main blood vessel at a point upstream of the branch point, with respect to the antegrade direction of blood flow;

inserting into the second blood vessel a first filter adapted to pass blood while trapping debris resulting from removal of the obstruction;

inserting an obstruction removal assembly into the first blood vessel and operating the assembly to at least partially break up the obstruction and produce debris;

after operating the obstruction removal assembly, withdrawing the obstruction removal assembly from the patient's body and then inserting into the first blood vessel a second filter adapted to pass blood while trapping debris that results from removal of the obstruction;

after inserting the first and second filters, restoring blood flow in the main blood vessel; and withdrawing the first and second filters from the patient's body together with trapped debris.

DETAILED DESCRIPTION OF THE INVENTION

Figure 1:
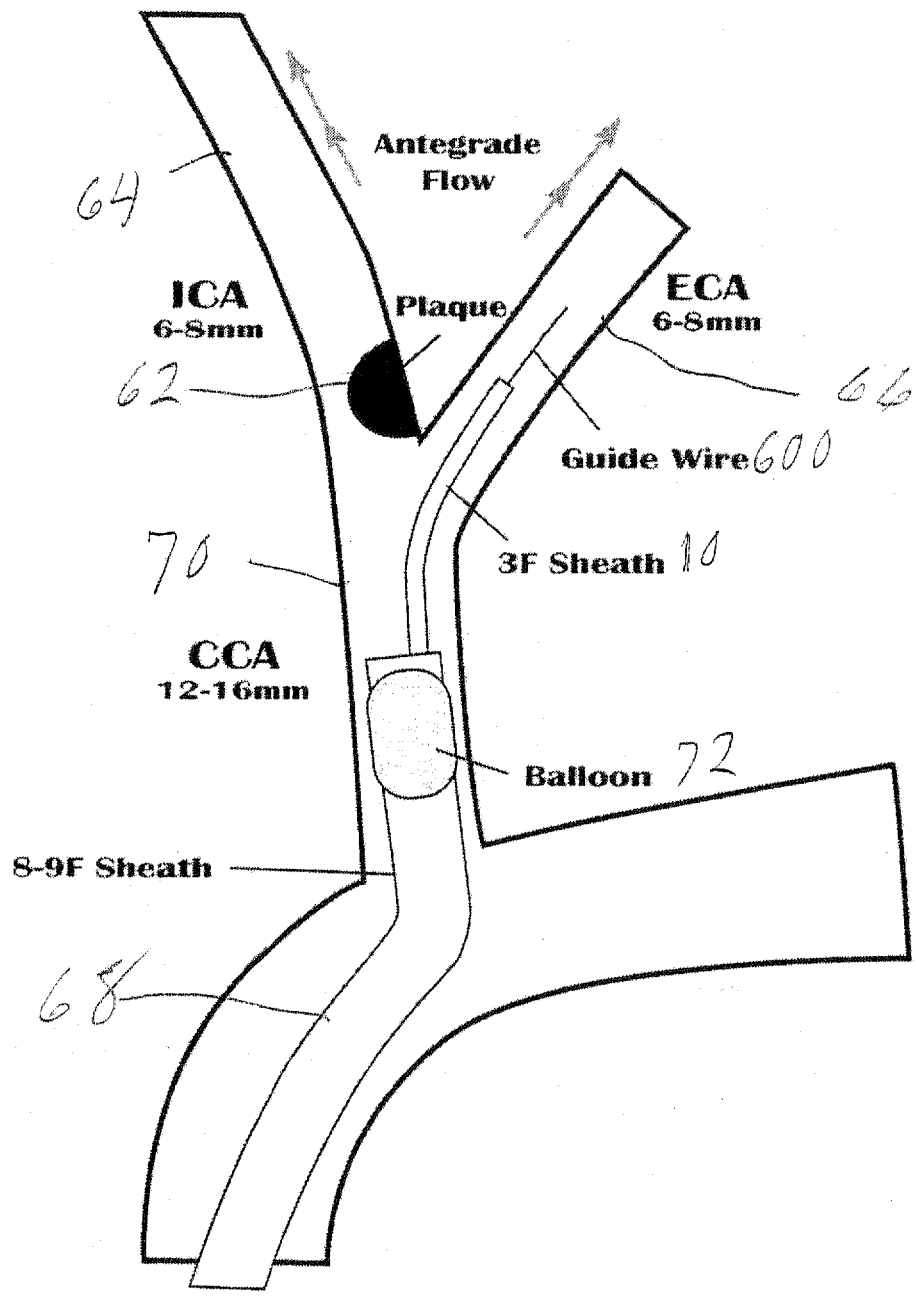
FIGS. 1-8 are pictorial views of successive stages in a procedure for treating an obstruction in a carotid artery according to the invention.

The advantages of the invention will become more apparent after reference to the following detailed description. In the practice of the present invention, use may optionally be made of filters described and illustrated in U.S. Pat. Nos. 6,485,502 and 7,214,237, the entire disclosures of which have been incorporated herein by reference. The following Figures show a device bearing certain similarities to that shown in FIG. 9 of U.S. Pat. Nos. 6,485,502 and 7,214,237 and having components shown in other Figures, and described in those patents. Components and body features identical to those of FIG. 9 and the other Figures will be identified herein with the same reference numerals as those used in FIG. 9.

The start of a procedure according to the invention is shown in FIG. 1. First, a sheath, or guiding catheter, 68 carrying a surrounding balloon 72 near its distal end is introduced into common carotid artery (CCA) 70 by a conventional angiographic procedure. Balloon 72 is initially deflated. Guiding catheter 68 preferably has a diameter of 8-9 Fr (3 Fr=1 mm).

The next step is the introduction of a filter into the external carotid artery. Customarily, the external carotid artery may have a tortuous course and its location is established initially by the use of a combination of a guide wire 600 and a sheath 10, which may have a diameter of 3 Fr. Guide wire 600 can be radiolucent and non-traumatic and can be positioned with the sheath accurately within the external carotid artery.

Figure 2:
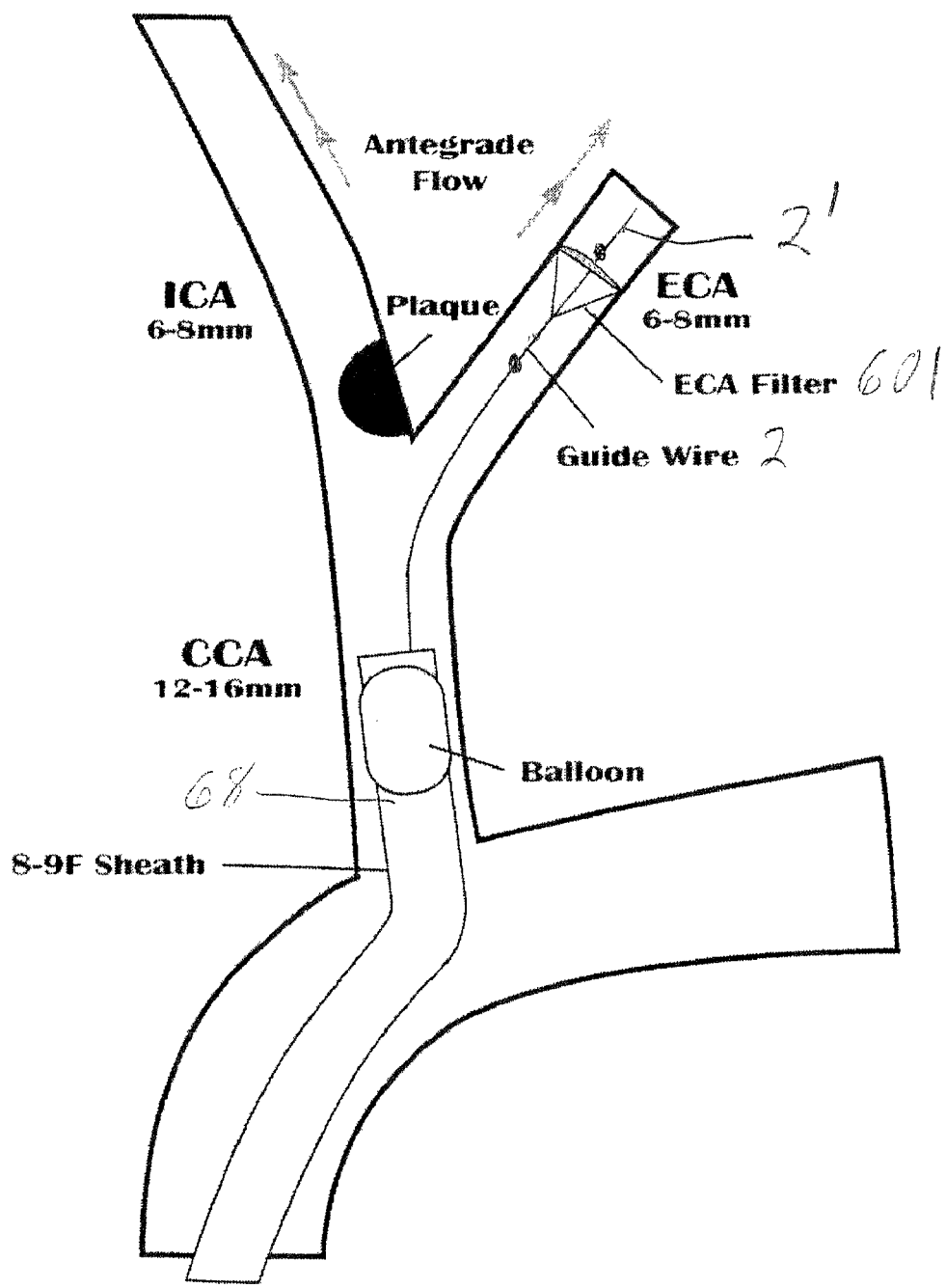

After this position has been established, guide wire 600 can be withdrawn and a filter 601 carried by a guide wire 2 having a distal extension 2' is placed in the external carotid artery 66 through sheath 10. Then sheath 10 is withdrawn to deploy, or expand, filter 601 in order trap any debris from the subsequent angioplasty procedure while allowing at least a limited blood flow past filter 601. This procedure is shown in FIG. 2. Guide wire 2 and extension 2' are each provided with a bead, as shown in FIG. 2, to hold filter 601 in place. Filter 601 may be provided with a filter sheet having a pore size of 100 μm.

At this stage, blood flow is antegrade, i.e., in the normal forward flow direction, in CCA 70, ICA 64 and ECA 66.

Filter 601 may have any of the forms shown in FIGS. 7 and 28-39 of U.S. Pat. Nos. 6,485,502 and 7,214,237.

Sheath 10 is withdrawn from the patient's body to assure that space is available in sheath 68 for subsequent insertion of other catheters.

Figure 3:
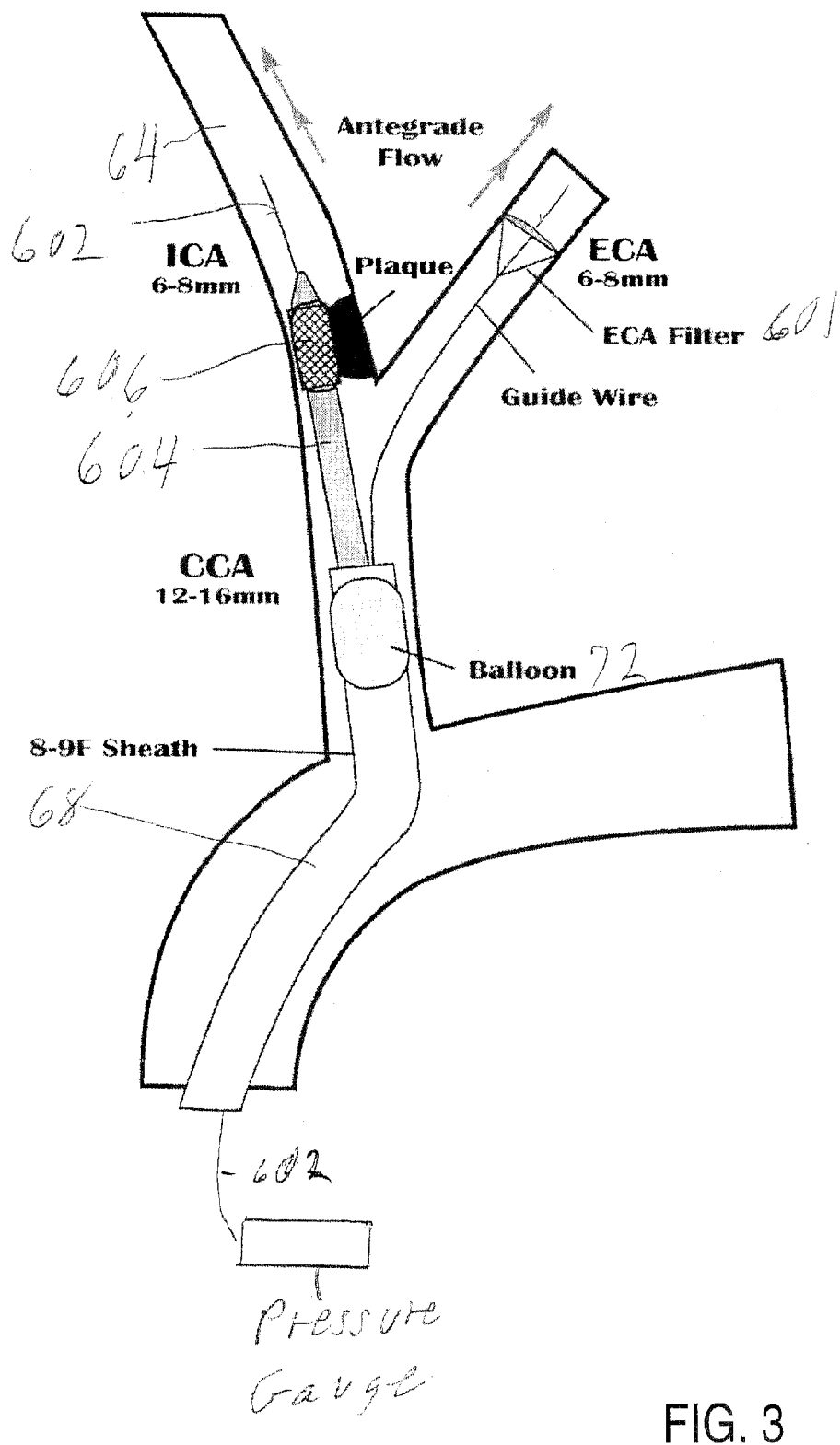

In the next part of the procedure, as shown in FIG. 3, a further guide wire 602 is introduced through sheath 68 into ICA 64, past the site of obstruction 62 and an angioplasty catheter 604 carrying a stent 606 is introduced over guide wire 602 to bring stent 606 in line with obstruction 62. For locating the internal carotid and dealing with technical difficulties of intubation this introduction may need to be carried out in exactly the same way as described above with respect to the introduction of filter 601 in ECA 66. Guide wire 602 can be a hollow guide wire connected to a pressure gauge to allow the pressure in ICA 64 to be monitored.

Catheter 604 typically carries a stent deployment balloon that is expanded after catheter 604 has been properly positioned, to expand and deploy stent 606 in order to alleviate the blockage caused by obstruction 62. Initially, the balloon carried by catheter 604 is deflated.

The blood flow continues to be antegrade.

Figure 4:
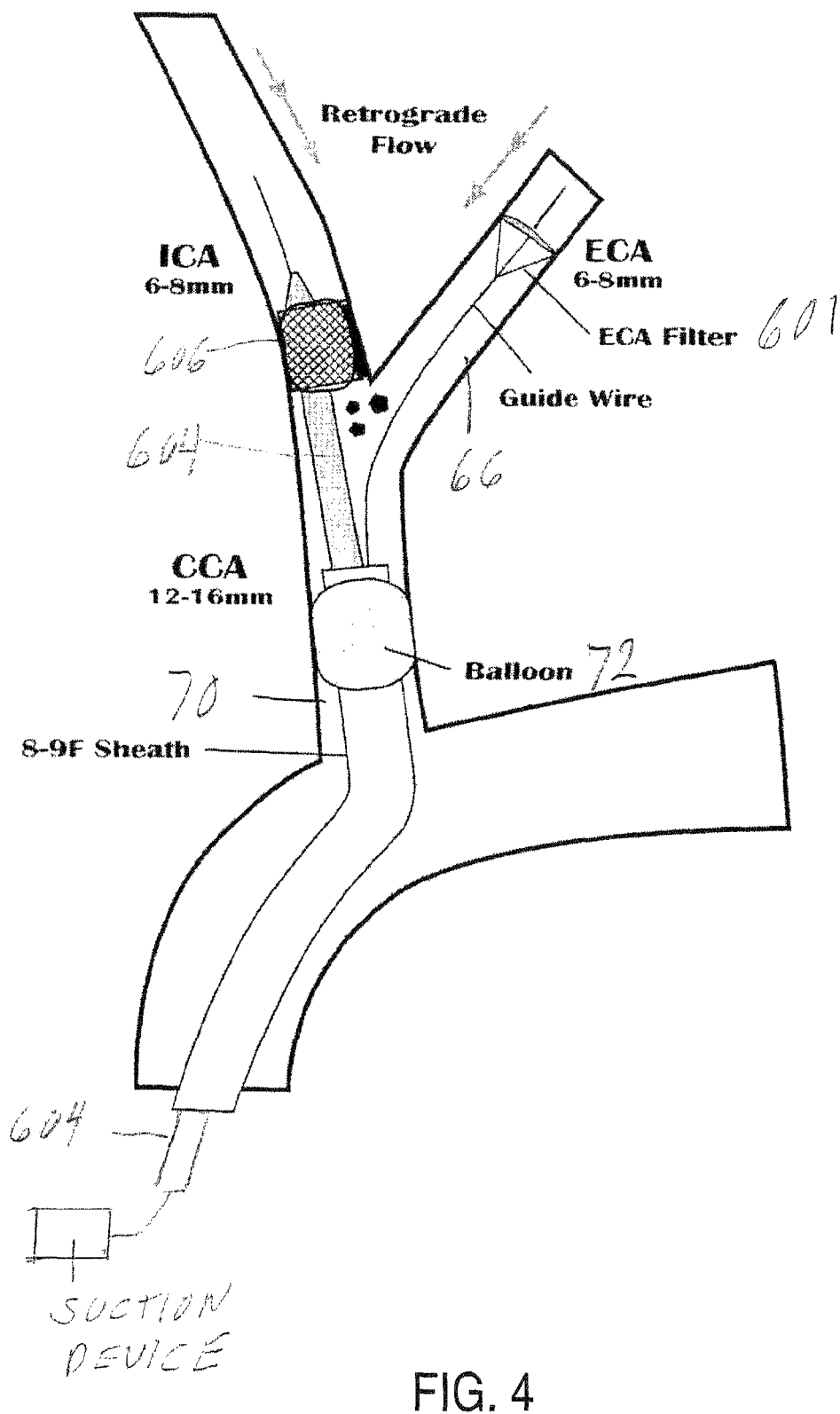

Then, as shown in FIG. 4, balloon 72 is inflated to block blood flow in CCA 70 around sheath 68, thereby essentially blocking most or all of antegrade blood flow in arteries 64, 66 and 70. This allows possible retrograde flow in the ICA and/or ECA. If at this time ICA 64 is not completely blocked, some retrograde flow may occur therein and will result in minimal antegrade flow into ECA 66. The reason for this assumption is that, ordinarily, blood flow, antegrade or retrograde, in an unobstructed ICA is approximately 3 times that into the ECA and the presence of a filter in the ECA would be expected to reduce flow through the ECA further. Hence, although the retrograde flow from the ICA will initially tend to stagnate in the intermediate part of the carotids between the ICA and ECA, one would expect that if flow occurs from the ICA to ECA, it would be minimal. Equally, the argument cant be made that in the presence of a high grade block in ICA 64, some minimal blood flow can occur from the ECA to ICA which, the presence of a filter, acting as a resistance and being used for this purpose, will tend to negate.

After inflation of balloon 72 to block blood flow in CCA 70 around sheath 68 (blood flow within sheath is prevented by sealing the proximal end of sheath 68), the balloon carried by catheter 604 is expanded to expand and deploy stent 606 in a manner to compress and at least partially disintegrate obstruction 62. The resulting debris tends to be trapped between filter 601 in ECA 66, balloon 72 and the balloon on catheter 604.

The balloon carried by catheter 604 is then deflated after stent deployment. It is to be noted that, ordinarily, retrograde flow would cease when CCA 70 is blocked. However, in the apparatus described, upon partial withdrawal of catheter 604, it can be utilized to perform low grade suction from outside the body of stagnant blood and debris in the area between the ICA, CCA and blocking balloon 72. Specifically, suction can be applied by a suction device connected to the proximal end of catheter 604, from a location outside of the patient's body, as shown in FIG. 4. If, for some reason, the suction provided through catheter 604 is inadequate, catheter 604 can be withdrawn completely from the patient's body and rapidly exchanged with a 6 F, non-tapered sheath inserted over guide wire 602 and advanced to the top of sheath 68. Controlled suction can then be resumed through that catheter into the suction device until particulate material and clots are evacuated. Furthermore, drugs such as heparin and other antithrombotic agents, for example Bivalarudin, can be introduced into the arteries through that catheter to allow any clots that have formed to be disintegrated. The drugs used can be other than the one mentioned but would need to be capable of clot dissolution. Using this technique of suction would also promote continued retrograde flow and avoid stagnation, and thereby, reduce the possibility of more clots forming. The material that is suctioned can be readily examined under a microscope and analyzed for debris size, content, and character. The reason for using low pressure suction is to prevent collapse of the stent or stents.

The presence of filter 601 in ECA 66 will markedly diminish retrograde flow and can serve to prevent a flow from ECA to ICA. Thus, it acts as a partial obstruction. For practical purposes, any retrograde flow from ICA 64 to ECA 66 will result in trapping of debris in filter 601.

Figure 5:
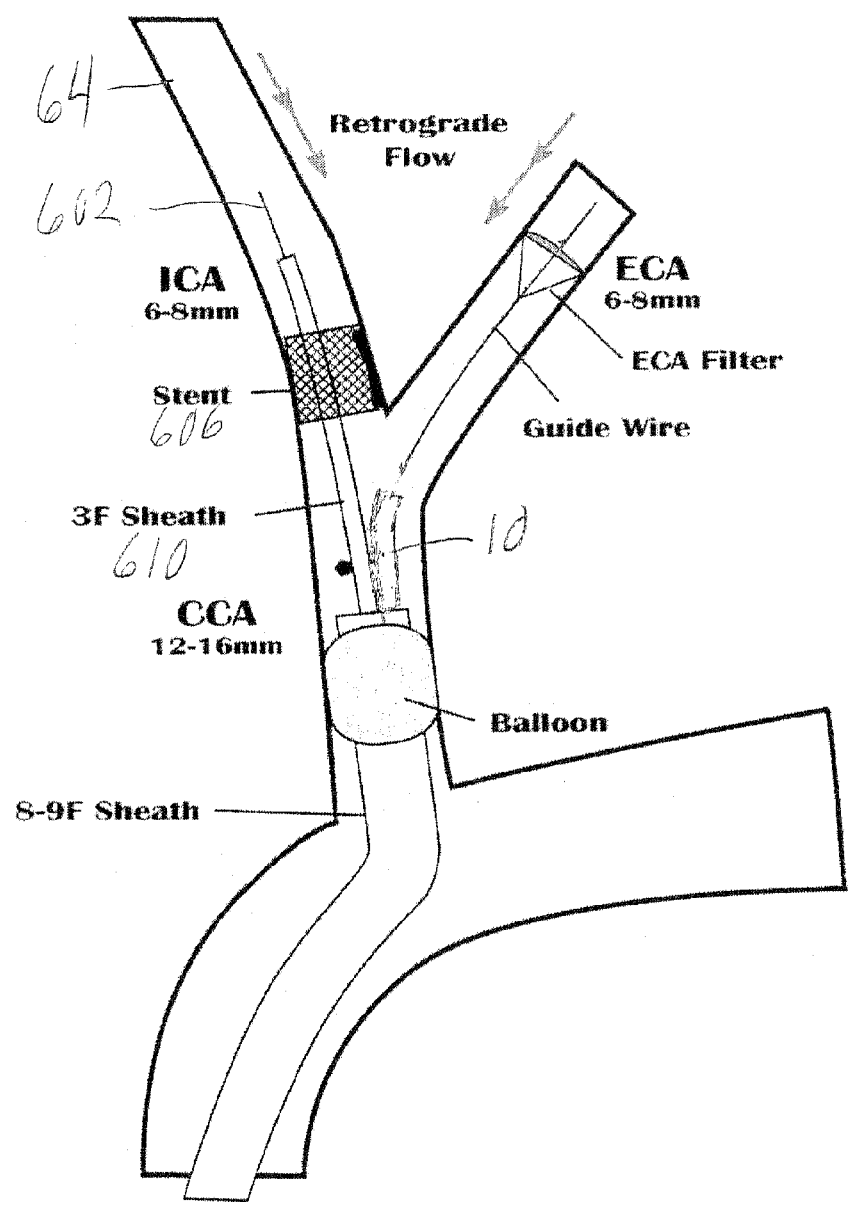
Figure 6:
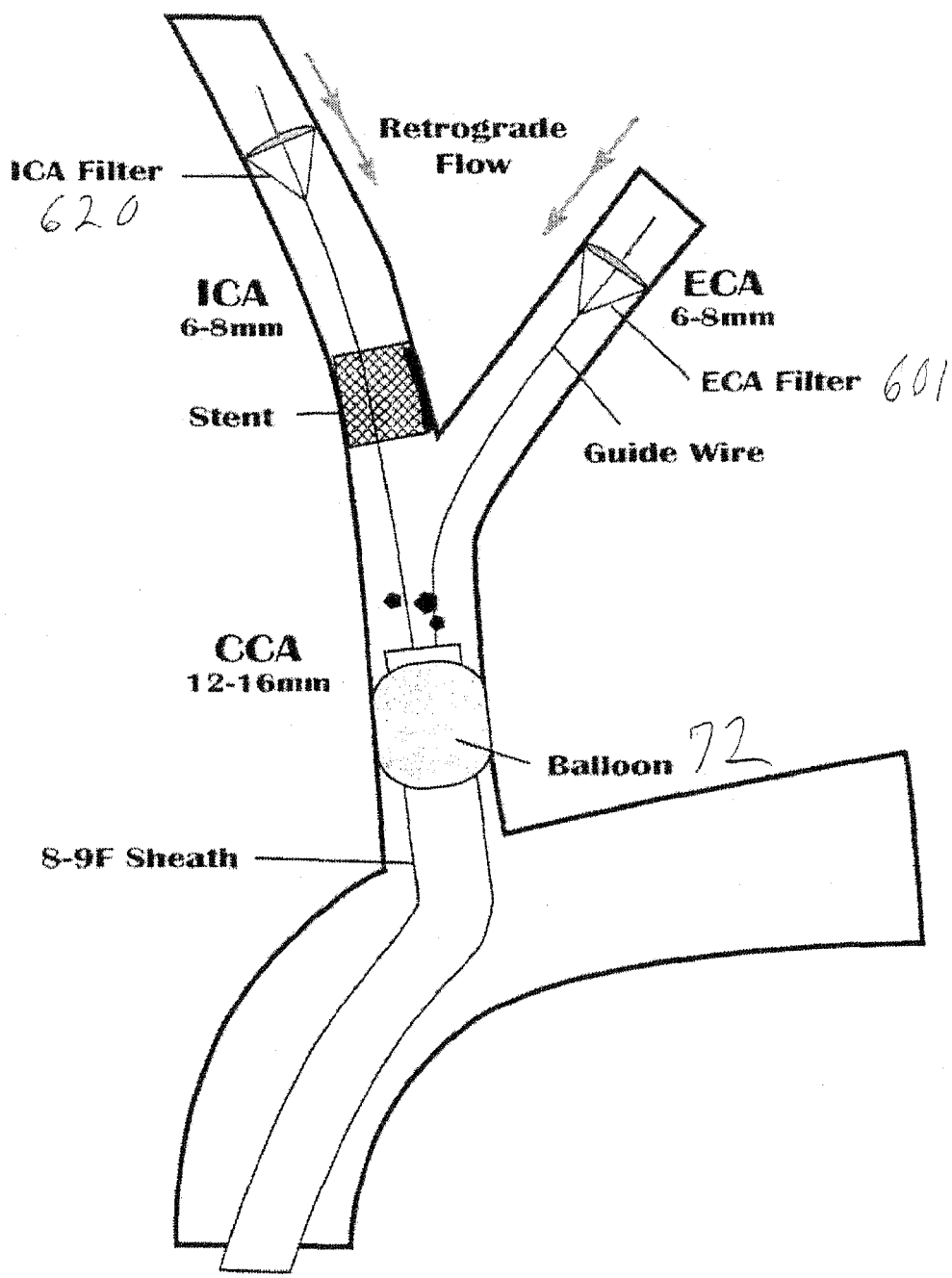

Then, angioplasty stent catheter 604, or the above-mentioned non-tapered sheath, is withdrawn from the patient's body and, as shown in FIG. 5, a 3 Fr sheath 610 is introduced into ICA 64 over guide wire 602 past stent 606. Guide wire 602 is then withdrawn from the patient's body and, as shown in FIG. 6, a second filter 620, identical to any of the filters disclosed herein, is introduced through sheath 610 by a procedure identical to that utilized for introducing a filter into the ECA, as described above, after which that sheath is pulled back to carefully deploy filter 620, using radiological verification beyond the stent, at a location past stent 606 and allow the filter to expand in order to trap any debris that may subsequently flow in the antegrade direction. In this stage, sheath 10 can be reintroduced at least into CCA 70, as shown in FIG. 5.

Sheath 610 can now be withdrawn or left in.

Figure 7:
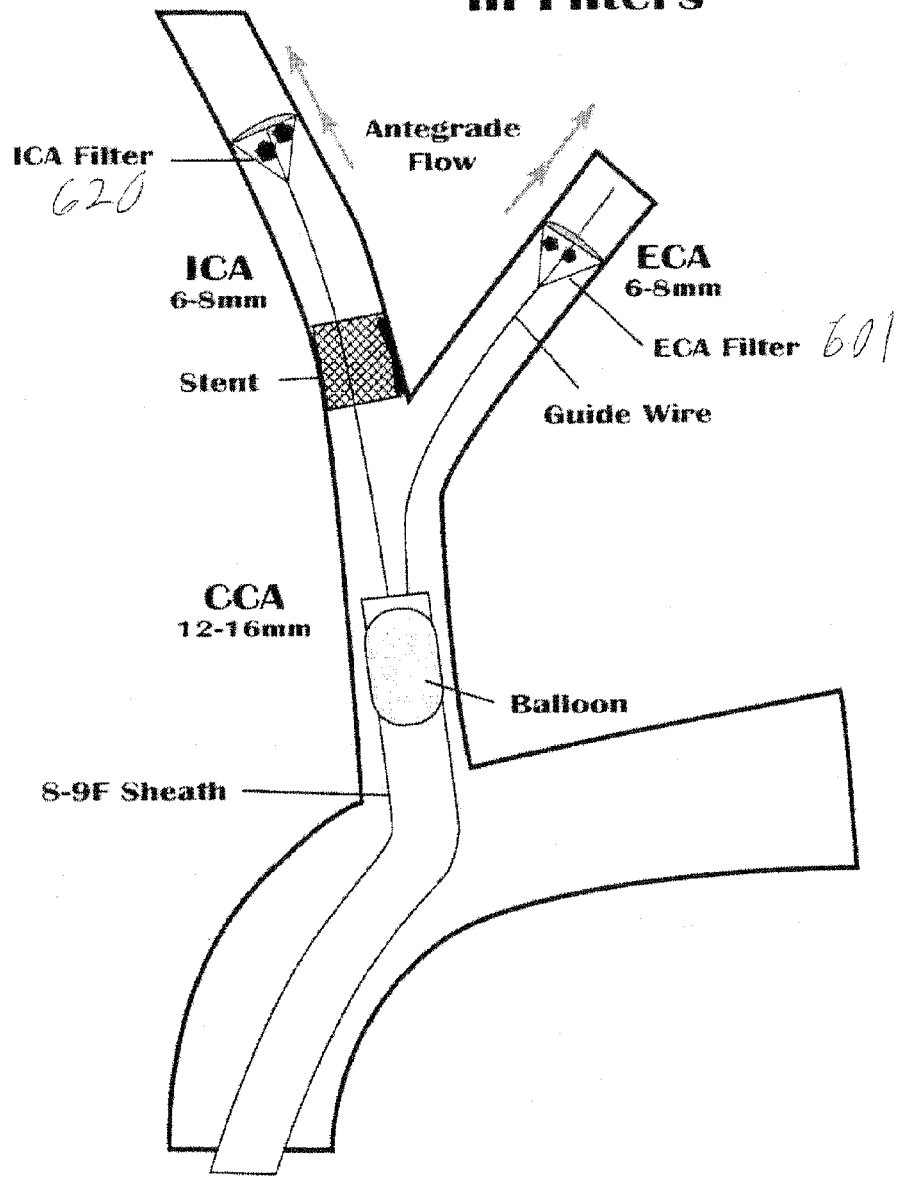
Figure 8:
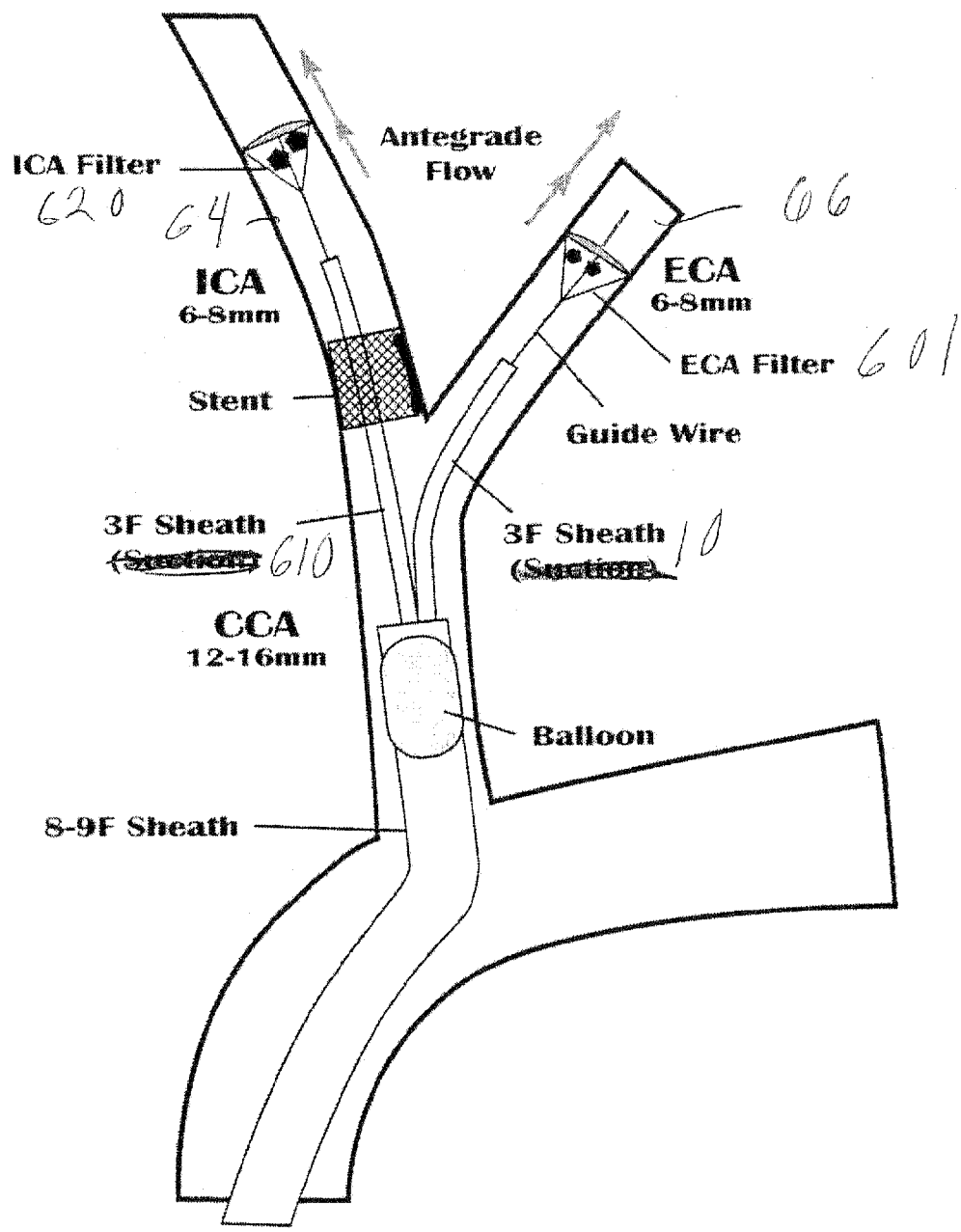

After both filters are safely deployed and are stable, antegrade flow is allowed to resume by deflating balloon 72. FIG. 7 shows debris captured by filters 601 and 620. The purpose of the two filters is to protect the cerebral circulation from embolization through either the internal carotid or, less commonly, through the external carotid, both arteries having been shown to have communications with the brain and the eyes.

If the patient is hemodynamically stable and has no evidence of stroke objectively determined by well known techniques such as transcranial doppler of the brain and clinical evaluation, each filter can be withdrawn using its respective introductory sheath to end the procedure. This is done, as shown in FIG. 48, by merely advancing, or reintroducing, sheaths 10 and 610 to capture and thus retract filters 601 and 620, filter 601 preferably being withdrawn first. Then sheaths 10 and 610 are completely removed from the patient's body, followed by withdrawal of sheath 68 from the patient's body.

According to a further feature of the invention, suction may be applied to ICA 64 through sheath 610 after angioplasty catheter 604 has been withdrawn from the patient's body, i.e., at the stage shown in FIG. 5, when balloon 72 is still inflated, and/or, through sheath 10 after it has been reintroduced at some point following withdrawal of catheter 604. This provides added assurance of complete removal of debris resulting from the angioplasty procedure.

Suction can also be applied directly through sheath 68.

Introduction of all illustrated components into the arteries can be effected according to conventional techniques through a conventional manifold.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for treating a patient having an obstruction on a wall of a first blood vessel through which blood normally flows in a given direction, at a location downstream of a branch point where the first blood vessel and a second blood vessel branch off from a main blood vessel, said method comprising:

blocking blood flow in the main blood vessel at a point upstream of the branch point, with respect to the antegrade direction of blood flow;

inserting into the second blood vessel a first filter adapted to pass blood while trapping debris resulting from removal of the obstruction;

inserting an obstruction removal assembly into the first blood vessel and operating the assembly to at least partially break up the obstruction and produce debris;

after operating the obstruction removal assembly, withdrawing the obstruction removal assembly from the patient's body and then inserting into the first blood vessel a second filter adapted to pass blood while trapping debris that results from removal of the obstruction;

after inserting the first and second filters, restoring blood flow in the main blood vessel; and withdrawing the first and second filters from the patient's body together with trapped debris.

2. The method of claim 1, wherein the first blood vessel is an internal carotid artery and the second blood vessel is an external carotid artery.

3. The method of claim 2 wherein the main blood vessel is a common carotid artery and said step of blocking blood flow is performed in the common carotid artery.

4. The method of claim 2 wherein said step of inserting a removal device obstruction comprises:
   introducing a guide wire through a guide catheter into the first blood vessel; and
   then introducing the removal assembly over the guide wire to the site of the obstruction.

5. The method of claim 1, further comprising, during a time when blood flow in the main blood vessel is blocked, applying suction to a region that contains debris produced from the obstruction.

6. The method of claim 5, wherein said step of applying suction is carried by operating a suction device located outside of the patient's body and placing the suction device in communication, through a tube, with the region that contains debris produced from the obstruction.

* * * * *